United States Patent [19]

Sawada et al.

[11] Patent Number: 5,061,624

[45] Date of Patent: Oct. 29, 1991

[54] SERINE ANALOGS OF BU-3608 ANTIBIOTICS

[75] Inventors: Yosuke Sawada, Tokyo; Masatoshi Kakushima, Yokohama; Maki Nishio, Tokyo; Takeo Miyaki; Toshikazu Oki, both of Yokohama, all of Japan

[73] Assignee: Bristol-Myers Company, New York, N.Y.

[21] Appl. No.: 569,679

[22] Filed: Aug. 20, 1990

Related U.S. Application Data

[62] Division of Ser. No. 269,821, Nov. 10, 1988, Pat. No. 4,973,673.

[51] Int. Cl.$^5$ .................... C12R 1/03; C12P 19/56
[52] U.S. Cl. ............................ 435/75; 435/170; 435/825; 536/6.4; 536/17.2; 536/18.1
[58] Field of Search .............. 435/75, 170, 825; 536/6.4, 17.2, 18.1

[56] References Cited

U.S. PATENT DOCUMENTS

| | | | |
|---|---|---|---|
| 4,546,084 | 10/1985 | Konishi et al. | 435/825 |
| 4,631,256 | 12/1986 | Koshiyama et al. | 435/825 |
| 4,780,416 | 10/1988 | Koshiyama et al. | 435/825 |
| 4,870,165 | 9/1989 | Oki et al. | 435/75 |
| 4,954,438 | 9/1990 | Yoshimoto et al. | 435/170 |
| 4,973,673 | 11/1990 | Sawada et al. | 435/75 |

*Primary Examiner*—Herbert J. Lilling
*Attorney, Agent, or Firm*—Mollie M. Yang

[57] ABSTRACT

Disclosed are antibiotics BU-3608 FA-1 and FA-2 and alkyl derivatives thereof. These compounds are useful as antifungal agents. BU-3608 FA-1 and FA-2 are produced from *Actinomadura hibisca* in a medium containing a source of D-serine.

1 Claim, 2 Drawing Sheets $^1$H-NMR OF BU-3608 FA-1 (400 MHz, DMSO-$d_6$)

$^1$H-NMR OF BU-3608 FA-2 (400 MHz, DMSO-$d_6$)

SERINE ANALOGS OF BU-3608 ANTIBIOTICS

CROSS REFERENCE

This application is a divisional of U.S. Ser. No. 269,821, filed Nov. 10, 1988, now U.S. Pat. No. 4,973,673, issued Nov. 27, 1990.

BACKGROUND OF THE INVENTION

The present invention relates to antifungal antibiotics, their production, their pharmaceutical use, and pharmaceutical compositions containing them. More particularly, the antibiotics are produced by *Actinomadura hibisca* and possess a benzo[a]naphthacene nucleus.

Few examples of benzo[a]naphthacene quinones derived from microbial sources have been reported and these include compounds designated G-2N and G-2A, and KS-619-1. While no biological activity was reported for G-2N and G-2A, KS-619-1 is disclosed as inhibitor of calcium ion and calmodulindependent cyclic nucleotide phosphodiesterase. Recently, published European Patent Application 277,621 discloses antifungal antibiotics BU-3608 (Ia), BU-3608 B (Ib), and BU-3608 C (Ic). Antibiotics benanomicins A and B were reported in J. Antibiotics, 1988, 41:807–811; benanomicin B appears to be the same as BU-3608 C whereas benanomicin A has a hydroxyl group in place of the sugar amino group.

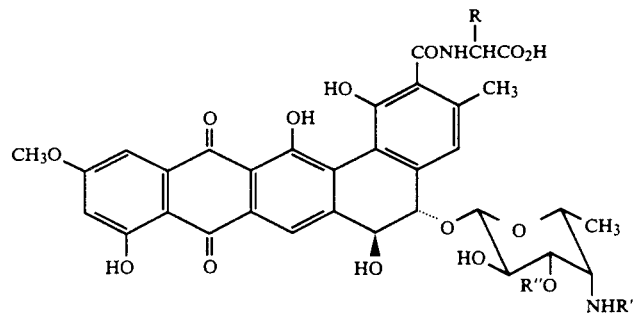

R = CH₃
Ia: R' = CH₃; R''-β-D-xylosyl
Ib: R' = CH₃; R'' = H
Ic: R' = H; R'' = β-D-xylosyl R = H
Id: R' = CH₃; R'' = β-D-xylosyl
Ie: R' = H; R'' = β-D-xylosyl Our co-pending application U.S. Ser. No. 203,776, filed June 7, 1988, now U.S. Pat. No. 4,992,425 discloses BU-3608 D (Id) and BU-3608 E (Ie).

SUMMARY OF THE INVENTION

The present invention provides compounds of the formula II

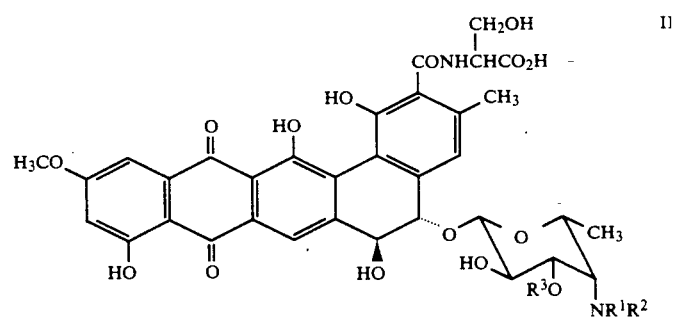

wherein the serine is D-serine; $R^1$ and $R^2$ are independently H or $C_{1-6}$alkyl; and $R^3$ is H or β-D-xylosyl; or a pharmaceutically acceptable salt thereof.

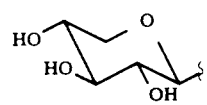

Another aspect of the present invention provides a process for preparing a compound of the formula III

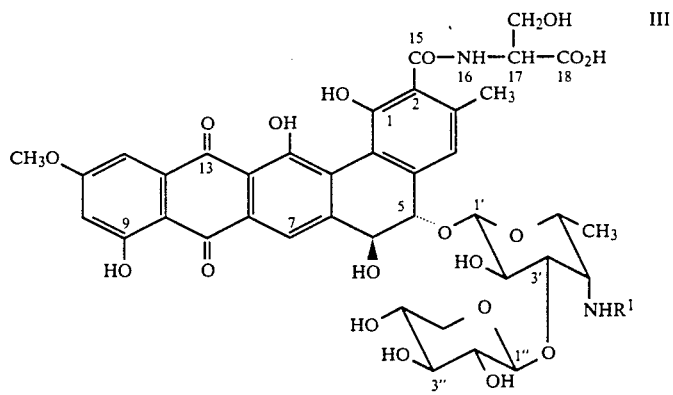

BU-3608 FA-1: $R^1$ = $CH_3$

BU-3608 FA-2: $R^1$ = H wherein $R^1$ is H or methyl, or a pharmaceutically acceptable salt thereof, which comprises cultivating a strain of *Actinomadura hibisca* capable of producing a compound of formula III in a medium containing assimilable sources of carbon and nitrogen, and D- or DL-serine under aerobic condition, and recovering said compound of formula III from the cultured broth.

A further aspect of the invention provides a pharmaceutical composition comprising a compound of formula II and a pharmaceutically acceptable carrier.

A further aspect of the invention provides a method for treating fungal infections in a mammalian host comprising administering an antifungal effective dose of a compound of formula II to said host.

Yet another aspect of the invention provides strains of *Actinomadura hibisca* capable of producing antibiotics of formula III in ammedium containing D- or DL-serine.

Also provided by the present invention is a compound having the formula IV or a salt thereof.

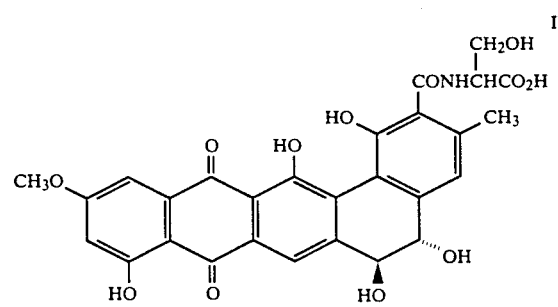

The compound of formula IV represents the aglycone of BU-3608 FA-1 and FA-2 and is useful in the synthesis of the parent antifungal agents or derivatives thereof.

DETAILED DESCRIPTION OF THE INVENTION

Figure 1:
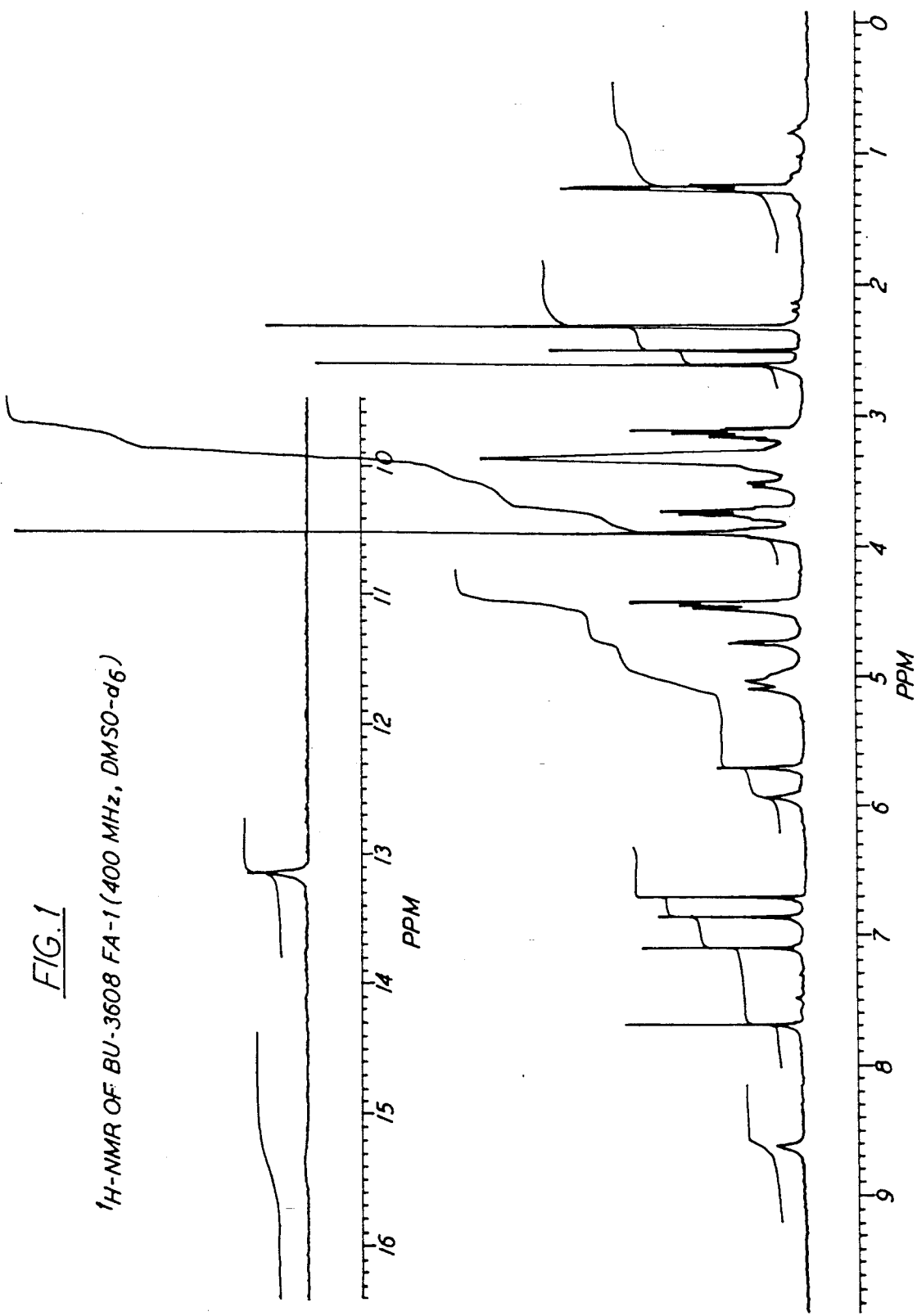
FIG. 1 represents a 400 MHz proton nuclear magnetic resonance spectrum of BU-3608 FA-1 in DMSO-$d_6$.

The antibiotics of the present invention are antifungal agents. Compounds of formula III, i.e. BU-3608 FA-1 and BU-3608 FA-2, are produced by cultivating a strain of *Actinomadura hibisca* capable of producing the antibiotics, or a variant thereof, or a mutant thereof, in a medium containing D- or DL-serine. As examples of antibiotic producing strains of *Actinomadura hibisca* mention can be made of strain P157-2 and mutant strains derived therefrom designated A2660, A2493 and B0012. Strain P157-2, which produces BU-3608 FA-1 preferentially in a medium supplemented with a source of D-serine, was isolated from a soil sample collected on Fiji Island in the South Pacific. A biologically pure culture of *Actinomadura hibisca* strain P157-2 has been deposited with the American Type Culture Collection in Rockville, Md. and added to their permanent collection of microorganism as ATCC 53557. Detailed description of the cultural and physiological characteristics of strain P157-2 is disclosed in our co-pending application Ser. No. 115,273 filed on Nov. 2, 1987, now U.S. Pat. No. 4,870,165, which is hereby incorporated by reference. The mutant strains A2660, A2493 and B0012, which are capable of producing both BU-3608 FA-1 and FA-2 in a medium containing a source of D-serine, were obtained from the parent strain P157-2 by exposing the parent strain to N-methyl-N'-nitro-N-nitrosoguanidine (1,000 μg/ml) for an hour; the strains were selected on the basis of their ability to produce BU-3608 antibiotic complex, i.e. BU-3608, or the B, C, D and E components, in the absence of added source of D-serine. Biologically pure cultures of A2660, A2493 and B0012 have been deposited with the ATCC and assigned the accession numbers 53762 (A2660), 53815 (A2493) and 53816 (B0012).

Cultural characteristics of the above-mentioned antibiotic producing strains of *Actinomadura hibisca* are provided in Table I.

TABLE I

| Cultural characterization of some producer strains | | | | |
|---|---|---|---|---|
| | Culture growth | | | |
| Media | P157-2 | A-2660 | A-2493 | B-0012 |
| Yeast extract-malt extract agar (ISP-2) | ++ | ++ | ++ | ++ |
| Glycerol-asparagine agar | + | ++ | − | ++ |

TABLE I-continued

| | Culture growth | | | |
|---|---|---|---|---|
| Media | P157-2 | A-2660 | A-2493 | B-0012 |
| (ISP-5) | | | | |
| Sucrose nitrate agar | + | + | − | ++ |
| Glucose-asparagine agar | ++ | ++ | − | ++ |
| D-Ribose | ++ | ++ | − | ++ |
| D-Glucose | ++ | ++ | − | ++ |
| Sucrose | + | + | − | ++ |
| Cellobiose | ++ | ++ | − | ++ |
| Trehalose | ++ | ++ | − | ++ |
| Sol. starch | ++ | ++ | − | ++ |
| Inositol | + | + | − | + |
| Salicin | + | + | − | + |
| L-Rhamnose | + | + | − | NT |
| D-Mannose | + | + | − | − |

++: Good growth
+: Growth
−: No growth
NT: not tested

It is to be understood that for the production of BU-3608 FA-1 and FA-2 the present invention is not limited to the particular organisms mentioned above, but includes the use of variants and mutants produced from these strains by various means such as x-ray radiation, UV-radiation and chemical mutagens. Other producers of antibiotics of the BU-3608 family and variants and mutants thereof capable of incorporating D-serine are also included.

The producing organism is grown in a nutrient medium containing a source of D-serine in addition to known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present application.

The nutrient medium should contain an appropriate assimilable carbon source such as ribose, glucose, sucrose, cellobiose. As nitrogen source, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron, and the like. As a source of D-serine, either D-serine or DL-serine may be used.

Production of antibiotics BU-3608 FA-1 and FA-2 may be effected at any temperature conducive to satisfactory growth of the producing organism, e.g. 25°–40° C. and is most conveniently carried out at a temperature of around 27°–32° C. Ordinarily, optimum antibiotic production is obtained in shake flasks after incubation periods of 5–8 days although a longer period may be necessary in certain cases. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture or a lyophilized culture of the organism. After obtaining an active inoculum in this manner, it is aseptically transferred to the fermentation tank medium. Antibiotic production in tank fermentors usually reaches the optimum after 3–6 days of incubation. Agitation in the tank fermentor is provided by stirring and aeration may be achieved by injection of air or oxygen into the agitated mixture. Antibiotic production may be monitored using chromatographic or spectroscopic techniques, or by a conventional biological assay.

Isolation and Purification of Antibiotics

The antibiotics of the present invention may be recovered from the cultivated broth by any suitable method for such recovery. A general scheme for one such method for the isolation and purification of antibiotics BU-3608 FA-1 and FA-2 from the fermentation broth is shown below as Scheme I.

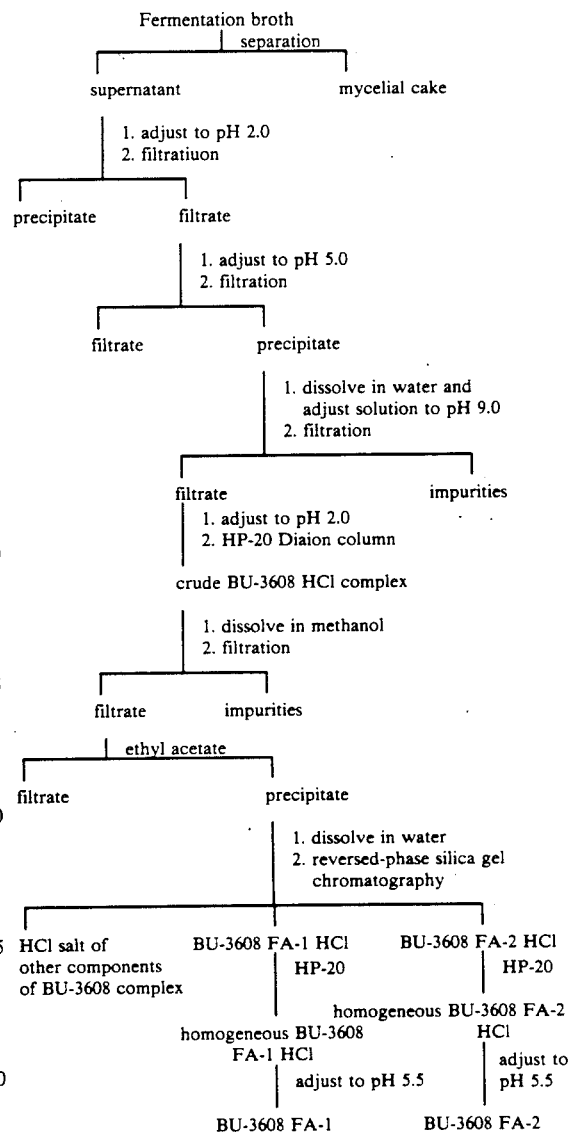

To elaborate on the flow chart of Scheme I, whole fermentation broth is separated into mycelial cake and supernatant by a conventional method such as centrifugation. The supernatant is acidified and the precipitate thus formed is removed. The filtrate is adjusted to pH 5 to deposit crude antibiotic which is redissolved in alkaline water and filtered to remove impurities. The filtrate is acidified to pH 2 and chromatographed on an adsorption column such as Diaion HP-20 to yield a crude BU-3608 HCl complex. The crude antibiotic complex may be recrystallized e.g. from ethyl acetate, and the product separated into individual antibiotic components using reversed phase silica gel HPLC. Fractions containing BU-3608 FA-1 and BU-3608 FA-2 may be further purified by Diaion HP-20 chromatography. The hydrochloride salts of the antibiotics may then be converted to the zwitterionic from by adjusting the pH of an aqueous solution of the HCl salt to pH 5.5.

Antibiotics BU-3608 FA-1 and FA-2 are characterized by the following physico-chemical properties.

in a similar fashion. It has been discovered that acid hydrolysis of N,N-dimethyl BU-3608 FA-2 results in a practical yield of the aglycone IV.

The amino group of BU-3608 FA-1, FA-2 or their corresponding desxylosyl derivatives may be alkylated by reductive alkylation which comprises first reacting the antibiotic starting material with an aldehyde or a ketone to form an imine, and subsequently reducing the imine thus formed. The condensation and reduction may be conducted in the same reaction vessel in one step, or in two separate steps. The primary amine group of BU-3608 FA-2 or its desxylosyl derivatives may be converted into a tertiary amine having two identical alkyl groups by treatment with at least two equivalents of the carbonyl compound relative to the antibiotic,

TABLE II

Figure 2:
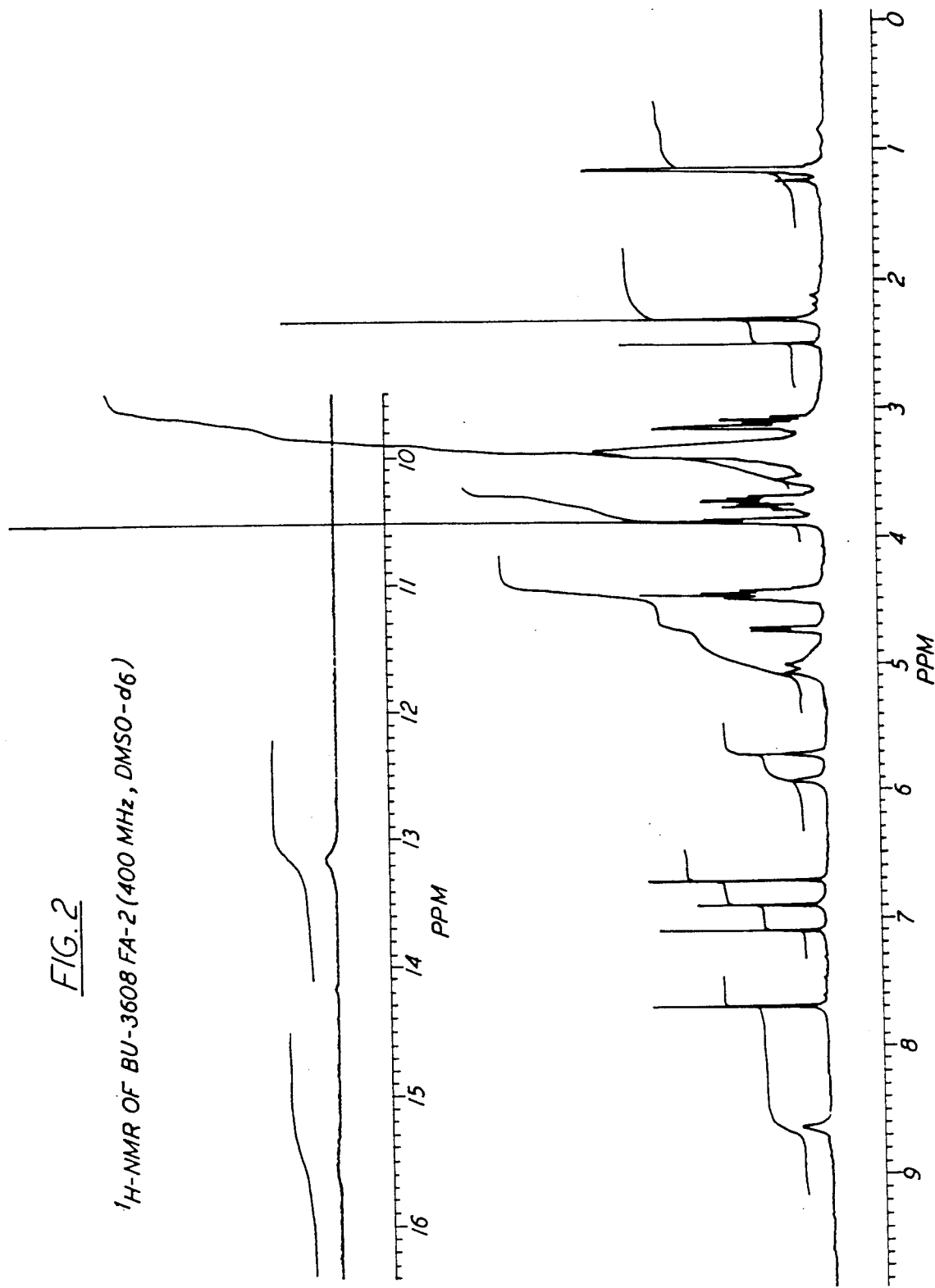
FIG. 2 represents a 400 MHz proton nuclear magnetic resonance spectrum of BU-3608 FA-2 in DMSO-$d_6$.

| Physico-chemical properties of BU-3608 FA-1 and FA-2 | | |
| --- | --- | --- |
| | BU-3608 FA-1 | BU-3608 FA-2 |
| Nature | Dark red amorphous powder | Dark red amorphous powder |
| M.P. (dec.) | 215–220° C. | 186–190° C. |
| $[\alpha]_D^{24}$ | +919° (c 0.1, 0.1N HCl) | +79° (c 0.1, 0.1N HCl) |
| SIMS m/z | 857 $(M + H)^+$ | 843 $(M + H)^+$ |
| Molecular formula | $C_{40}H_{44}N_2O_{19}$ | $C_{39}H_{42}N_2O_{19}$ |
| $^1$H NMR | substantially as shown in FIG. 1 | substantially as shown in FIG. 2 |
| $^{13}$C NMR (100 MHz DMSO-d$_6$) | 16.3(q), 20.3(q), 36.4(q), 54.9(d), 56.1(q), 61.6(t), 63.1(d), 65.9(q), 67.8(d), 69.3(d), 69.9(d), 71.7(d), 73.6(d), 75.8(d), 80.5(d), 82.1(d), 104.1(d), 104.2(d), 105.2(d), 106.0(d), 110.3(s), 111.4(d), 117.1(d), 119.0(s), 119.2(s), 126.3(s), 132.1(s), 133.0(s), 136.8(s), 137.6(s), 137.9(s), 143.5(s), 158.0(s), 163.6(s), 165.8(s), 166.2(s), 168.5(s), 172.2(s), 180.2(s), 187.3(s) | 16.4(q), 20.4(q), 55.0(d), 56.2(q), 61.7(t), 54.3(d), 65.9(q), 67.3(d), 69.4(d), 69.7(q), 71.8(d), 73.5(d), 75.9(d), 79.1(d), 82.5(d), 104.2(d), 104.3(d), 105.1(d), 106.1(d), 110.4(s), 111.5(d), 117.2(d), 119.1(s), 119.3(s), 126.3(s), 132.1(s), 133.1(s), 136.8(s), 137.8(s), 138.0(s), 143.5(s), 158.2(s), 163.7(s), 165.8(s), 166.2(s), 168.6(s), 172.3(s), 180.1(s), 187.4(s) |
| UV$_{\lambda max}$nm ($\epsilon$) | | |
| in 50% MeOH | 221(32,100), 276(27,400) 499(12,900) | 223(27,700), 277(25,400) 499(12,200) |
| in 0.01N HCl-50% MeOH | 234(37,400), 299(31,100) 460(12,900) | 234(34,500), 296(28,900) 460(12,000) |
| in 0.01N NaOH-50% MeOH | 244(34,100), 320(15,700) 498(14,900) | 233(37,200), 319(16,600) 498(15,100) |
| IR (KBr)cm$^{-1}$ | 3400, 2920, 1605, 1385, 1295, 1260, 1160, 1040 | 3400, 2920, 1600, 1385, 1295, 1255, 1160, 1040 |
| TLC SiO$_2$ Rf (S-114, MeOAc-n-PrOH-28% NH$_4$OH = 45:105:60, v/v) | 0.26 | 0.22 |
| HPLC Rt (min) (ODS, CH$_3$CN-0.15% KH$_2$PO$_4$, pH 3.5 (25:75) | 8.61 | 7.65 |

Antibiotics BU-3608 FA-1 and FA-2 may be subjected to further chemical modification. Heating BU-3608 FA-1, FA-2, or a mixture thereof in an acidic medium for a period sufficient to cleave the xylosyl group provides the corresponding desxylosyl derivatives and small amounts of the aglycone IV. The solvent used may be for example dioxane, tetrahydrofuran, water, lower alkanol, or mixtures thereof; acid catalyst may be for example hydrochloric acid, sulfuric acid, and trifluoroacetic acid. The temperature may be from about 60 to about 100° C, or the reflux temperature of the solvent. Reaction time may be from about 0.5 to about 10 hrs and will depend on the reaction conditions employed. N,N-dimethyl BU-3608 FA-2, prepared by reductive alkylation procedure described below, may be converted to its corresponding desxylosyl compound followed by reduction; or a tertiary amine having two different alkyl substituents may be obtained by using a controlled amount of a first carbonyl reactant to convert the primary amine into a secondary amine which is then reacted with a second different carbonyl compound to give the product tertiary amine. If the second carbonyl compound is not added, a secondary amine is obtained.

The carbonyl reactant may be an aldehyde or a ketone having one to six carbon atoms, for example, formaldehyde, acetaldehyde, propionaldehyde, and acetone. Reduction of the imine may be accomplished by using reducing agents such as metal hydrides, for example, sodium borohydride, sodium cyanoborohydride, lithium aluminum hydride. The reaction is carried out in a polar organic solvent or a mixture thereof such as water, acetonitrile, lower alkanols, and dimethyl sulfoxide. The reaction temperature is not particularly restricted and may be from room temperature to about 100° C. In our experience, the alkylation reaction carried out at room temperature is usually complete within 24 hours. Optimum reaction conditions will of course depend on the nature and reactivity of the particular reactants used. It will be appreciated that N,N-dimethyl BU-3608 FA-2 may be obtained from BU-3608 FA-2, FA-1, or a mixture thereof without having to separate the two components. Similarly, N,N-dimethyl desxylosyl BU-3608 FA-2 may be obtained from desxylosyl BU-3608 FA-2, FA-1, or a mixture thereof.

Biological Activity

Antifungal activities of representative compounds of the present invention were evaluated both in vitro and in vivo. The minimum inhibitory concentrations (MICs) against various fungi were determined by serial agar dilution method using Sabouraud dextrose agar. Thus, approximately 0.003 ml of fungal suspension containing $10^6$ cells/ml was applied to the surface of agar plates containing the test antibiotics. The MIC values recorded after the cultures had been incubated for 40 hours at 28° C. are set forth below in Table III.

died within 7 to 15 days after fungal infection. The results of in vivo studies are presented in Table IV.

TABLE IV

| | In vivo activity against *Candida*, *Cryptococcus* and *Aspergillus* intravenous infections $PD_{50}$ (mg/kg/inj. iv) | | | | | |
|---|---|---|---|---|---|---|
| | *C. albicans* A9540 | | *C. neoformans* IAM4514 | | *A. fumigatus* IAM2034 | |
| | Single | qd × 5 | Single | qd × 5 | Single | qd × 5 |
| BU-3608 FA-1 | 18 | — | — | — | — | — |
| BU-3608 FA-2 | 7.4 | — | — | — | — | — |
| N,N-dimethyl BU-3608 FA-2 | 9.0 | 7.5 | 11 | 2.8 | 36 | 15 |

The $LD_{50}$ for N,N-dimethyl BU-3608 FA-2 was determined in mice after a single intravenous dose. At 600 mg/kg, the highest dose test, neither lethal toxicity nor any significant toxic sign was observed.

For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration.

TABLE III

| | In vitro antifungal activity in Sabouraud dextrose agar (pH 7.0) | | | | | |
|---|---|---|---|---|---|---|
| | MIC (µg/ml) | | | | | |
| Test organism | BU-3608 FA-1 | BU-3608 FA-2 | N,N-dimethyl BU-3608 FA-2 | Des-xylosyl BU-3608 FA-1 | Des-xylosyl BU-3608 FA-2 | Des-xylosyl N,N-dimethyl BU-3608 FA-2 |
| *Candida albicans* IAM4888 | 6.3 | 6.3 | 3.1 | 3.1 | 3.1 | 6.3 |
| *C. albicans* A9540 | 12.5 | 6.3 | 6.3 | 3.1 | 3.1 | 6.3 |
| *Cryptococcus neoformans* D49 | 0.8 | 0.8 | 0.8 | 1.6 | 3.1 | 1.6 |
| *C. neoformans* IAM4514 | 0.8 | 0.8 | 0.8 | 1.6 | 3.1 | 1.6 |
| *Aspergillus fumigatus* IAM2530 | 3.1 | 3.1 | 3.1 | 6.3 | 12.5 | 6.3 |
| *A. fumigatus* IAM2034 | 6.3 | 6.3 | 3.1 | 6.3 | 12.5 | 6.3 |
| *A. flavus* FA21436 | 6.3 | 6.3 | 25.0 | 50 | 50 | 12.5 |
| *Fusarium moniliforme* A2284 | 6.3 | 6.3 | 25.0 | >100 | >100 | 50 |
| *Trichophyton mentagrophytes* D155 | 6.3 | 6.3 | 12.5 | 12.5 | 12.5 | 6.3 |
| *T. mentagrophytes* #4329 | 6.3 | 6.3 | 6.3 | 12.5 | 12.5 | 6.3 |
| *Blastomyces dermatitidis* D40 | 3.1 | 3.1 | 6.3 | 6.3 | 6.3 | 3.1 |
| *Sporothrix schenckii* IFO8158 | 1.6 | 1.6 | 1.6 | 6.3 | 6.3 | 3.1 |
| *Petriellidium boydii* IFO8073 | 12.5 | 25 | ND | >100 | >100 | 100 |
| *Mucor spinosus* IFO5317 | >100 | >100 | ND | 12.5 | 25 | 25 |

ND: Not determined

In vivo antifungal activities were evaluated against intravenous infections with *Candida albicans* A9540, *Cryptococcus neoformans* IAM4514 and *Aspergillus fumigatus* IAM2034 in mice. *Candida albicans* and *Cryptococcus neoformans* were cultured for 18 and 48 hours, respectively, at 28° C. in YGP medium [yeast extract(0.2%), glucose(1.5%), peptone(0.5%), $K_2HPO_4$(0.05%) and $MgSO_4$(0.05%)]and suspended in saline. *Aspergillus fumigatus* was cultured for 7 days at 28° C. on YGP agar slant and suspended in saline. Spores were collected by filtering fungal suspension through gauze. Male ICR mice weighing 20 to 24 g were infected intravenously with about 10 times the median lethal dose of the fungi.

Test compounds were administered at various doses to groups of 5 mice each intravenously either once just after fungal challenge (day 0) or once daily for 5 days from day 0 to day 4 (qd×5). The 50% protective dose ($PD_{50}$) was calculated from survival rates recorded on the 20th day after fungal challenge. All control animals Preparations for parenteral administration include sterile aqueous or non-aqueous solutions, suspensions or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that when treating a host infected with a fungus susceptible to the antibiotics of this invention, the actual preferred route of administration and dosage used will be at the discretion of the attending clinician skilled in the treatment of fungal infections, and will vary according to the causative organism, its sensitivity to the antibiotic, severity and site of the infection, and patient characteristics such as age, body weight, rate of excretion, concurrent medications, and general physical condition.

The following examples are illustrative without limiting the scope of the present invention.

EXAMPLE 1

Fermentation Production Of BU-3608 FA-1

(a) Agar Slant

*Actinomadrua hibisca* P157-2 (ATCC 53557) was grown on an agar slant of pH 7.0 having the composition
0.5% soluble starch
0.5% glucose
0.1% fish meat extract
0.1% yeast extract
0.2% NZ-case
0.2% NaCl
0.1% $CaCO_3$
1.6% agar The culture was incubated at 28° C. for 10 days.

(b) Seed Culture

A portion of the microbial growth from the slant culture was transferred to a 500-ml Erlenmeyer flask containing 100 ml of vegetative medium pH 7.0 composed of
3% glucose
3% soybean meal
0.5% Pharmamedia
0.1% yeast extract
0.3% $CaCO_3$ The culture was incubated at 32° C. for 6 days on a rotary shaker set at 200 rpm.

(c) Production Culture

Five ml of the microbial growth was transferred from the seed culture to a 500-ml Erlenmeyer flask containing 100 ml of sterile production medium composed of
3% glucose
3% soybean meal
0.5% Pharmamedia
0.1% yeast extract
0.3% $CaCO_3$
0.25% D-serine The culture was incubated at 28° C. for 6 days on a rotary shaker set at 200 rpm. Antibiotic production reached 443 μg/ml and 72.9% of which was BU-3608 FA-1, 26.0% BU-3608 and 1.1% BU-3608C. Antibiotic production was determined by measuring the optical density of the liquid from the fermentation broth at 500 and 600 nm. Genuine optical density was obtained by substracting the OD value at 600 nm from that at 500 nm. Antibiotic concentration is expressed as equivalent amount of BU-3608 free base. The antibiotics were identified using the HPLC procedure described in Example 5.

EXAMPLE 2

Fermentation Production Of BU-3608 FA-1 and FA-2 Using Strain A-2493

Agar slant culture and seed culture of an arginine auxotroph mutant of *Actinomadura hibisca* P157-2 designated as strain A-2493 (ATCC 53815) were grown using media having the same compositions as those described in Example 1 and under conditions given in Example 1.

Production A

Five ml of the microbial growth was transferred from the seed culture to each 500-ml Erlenmeyer flask (100 flasks) containing 100 ml of the same production medium described in Example 1(c) The culture was incubated at 28° C. for 6 days on a rotary shaker set at 200 rpm. Antibiotic production reached 261 μg/ml and was composed of 29.8% BU-3608 FA-1, 28.9% BU-3608 FA-2, 19.5% BU-3608C and 21.8% BU-3608.

Production B

Production of antibiotics by strain A2493 was also effected in a medium (pH 7.0) composed of
3% glucose
3% Protein S (soybean flour, Ajinomoto)
0.3% $CaCO_3$
0.5% DL-serine Antibiotic production reached 890 μg/ml after the culture had been incubated for 11 days at 28° C. The ratio of components was BU-3608 FA-2 17.7%, FA-1 17.0%, BU-3608 33.5% and BU-3608 C 31.8%.

EXAMPLE 3

Fermentation Of BU-3608 FA-1 And FA-2 Using Strain B-0012

Production A

The conditions and culture media described in Example 1 parts (a), (b) and (c) were followed using the variant strain designated B-0012 (ATCC 53816) instead of the parent strain P157-2. Antibiotic production reached 1,150 μg/ml after 6 days and the ratio of components was BU-3608 FA-1 33.7%, FA-2 21.2%, BU-3608 24.0% and BU-3608 C 21.1%.

Production B

A portion of microbial growth from the slant culture of strain B-0012 was also transferred to a 500-ml Erlenmeyer flask containing 100 ml of a medium pH 7.0 having the following composition
1% soluble starch
1% glucose
0.5% Yeast extract
0.5% peptone
0.3% NaCl
0.2% $CaCO_3$ The seed culture was grown at 32° C. for 6 days and 5 ml of the microbial growth was transferred to a 500-ml Erlenmeyer flask containing 100 ml of a production medium pH 7.0 composed of
3% glucose
3% Protein S (soybean flour, Ajinomoto)
0.3% $CaCO_3$
0.25% D-serine The culture was incubated at 28° C. for 11 days. Antibiotic production reached 1,970 μg/ml and the ratio of components was BU-3608 FA-2 20.0%, FA-1 10.0%, BU-3608 C 39.0% and BU-3608 31.0%.

EXAMPLE 4

Fermentation Production Of BU-3608 FA-1 and FA-2 Using Strain A-2660

Agar slant and seed cultures of *Actinomadura hibisca* mutant strain A-2660 (ATCC 53762) were produced using the same conditions and media given in Example 1 parts (a) and (b). Five ml of the seed culture was transferred to a 500-ml Erlenmeyer flask containing 100 ml of a production medium composed of 3% glucose
3% soybean meal
0.5% Pharmamedia
0.1% yeast extract
0.3% $CaCO_3$
0.5% DL-serine The culture was incubated at 28° C. for 7 days. Antibiotic production reached 620 μg/ml with the ratio of components as BU-3608 FA-1 17.0%, FA-2 15.6%, BU-3608 23.9%, BU-3608 C 24.7%, D 8.3% and E 10.5%.

EXAMPLE 5

Isolation And Purification of BU-3608 FA-1 And FA-2 From Fermentation Broth

Ten liters of fermentation broth obtained from the procedure described in Example 2, Production A, was separated into mycelial cake and supernatant by centrifugation. The supernatant was acidified to pH 2.0 using 6N HCl and the amorphous precipitate deposited was removed by filtration. The clear filtrate was adjusted to pH 5.0 using 6N NaOH, and kept at 5° C. for two hours. The dark red precipitate deposited was collected by filtration. The precipitate was dissolved in 4.1 L of water adjusted to pH 9.0 with 6N NaOH and the solution was filtered to remove insoluble impurities. The filtrate was adjusted to pH 2.0 and applied on a column of Diaion HP-20 (2.0 L). The column was washed with water and eluted with 60% aqueous acetone (pH 3.0). Concentration of the red eluate afforded amorphous solid of BU-3608 complex hydrochloride (3.1 g). The complex solid (3.0 g) was dissolved in methanol (120 ml) and filtered. To the stirred filtrate, 720 ml of ethyl acetate was added dropwise and the resulting solution was kept at 5° C. for 15 hours. The precipitate deposited was collected by filtration and dried (1.28 g).

The solid (1.28 g) was dissolved in water (100 ml) and subjected to reversed phase chromatography on a column of YMC GEL ODS A 60 (10 L, Yamamura Chemical Lab.) which had been equilibrated with a mixture of $CH_3CN$-0.15% $KH_2PO_4$, pH 3.5 (21:79). Elution was carried out with the same solvent mixture, and the eluate was collected in 1L-fractions. The fractions were analyzed by HPLC (column : YMC A-301-3, 4.6 mm I.D.×100 mm, 3μm, ODS Yamamura Chemical Lab., mobile phase : $CH_3CN$-0.15% $KH_2PO_4$, pH 3.5 (25:75), flow rate : 0.8 ml/min, detection : UV absorption at 254 nm, retention time : BU-3608 FA-2, 7.65 min; BU-3608 FA-1, 8.61 min ; BU-3608A, 19.11 min). The fractions containing homogeneous BU-3608 FA-2 or BU-3608 FA-1, were pooled and concentrated in vacuo to remove $CH_3CN$. Each concentrate was desalted by Diaion HP-20 chromatography to yield nearly homogeneous BU-3608 FA-2 hydrochloride (75 mg) and BU-3608 FA-1 hydrochloride (50 mg).

In order to convert the hydrochloride salt to its free form and to remove contaminated inorganic salts, an aqueous solution of each salt was adjusted to pH 5.5 with 0.1N NaOH to deposit pure zwitterionic form of BU-3608 FA-2 (48 mg) and BU-3608 FA-1 (11 mg).

EXAMPLE 6

Preparation Of N,N-dimethyl BU-3608 FA-2

A mixture of BU-3608 FA-1 and BU-3608 FA-2 (45:55, 510 mg) was dissolved in 50 ml of water and the solution was adjusted to pH 7.9 by addition of 1N sodium hydroxide and diluted with 50 ml of acetonitrile. To this solution were added sequentially aqueous formaldehyde (>35%, 1.6 ml) and sodium cyanoborohydride (240 mg) at room temperature. The solution was stirred for 1 hour at room temperature and the progress of reaction monitored by HPLC. The organic solvent was removed in vacuo and the aqueous residue was adjusted to pH 10.9. The solution (40 ml) was added dropwise to 240 ml of acetone with stirring and kept at 5° C. for 2 hours. The resulting precipitate was collected by centrifugation (3000 rpm) and redissolved in 40 ml of water. After removal of traces of the acetone in vacuo, the solution was adjusted to pH 5.0 and allowed to stand at 5° C. for 24 hours. The precipitate deposited was collected by centrifugation, washed sequentially with water and acetone, and vacuum-dried at 60° C. to afford 80 mg of zwitterionic N,N-dimethyl FA-2. M.p. 214°–218° C. (dec.); $UV\lambda_{max}^{0.01N\ NaOH}$ nm(ε) 232.8 (32,900), 320.0(15,500), 498.4(15,200).

EXAMPLE 7

Preparation Of Desxylosyl BU-3608 FA-1

A solution of BU-3608 FA-1 (54 mg) in dioxane (5.4 ml) and 1N HCl (5.4 ml) was refluxed on a steam bath for 8 hr. The reaction mixture was diluted with water (30 ml) and charged on a short column of Diaion HP-20 (Mitsubishikasei, 1.8×25 cm). The column was washed with water and then eluted with acidic 80% acetone (pH 3, acidified with 1N HCl). The reddish orange eluate was collected and evaporated to give a deep red powder. The powder was dissolved in 35% acetonitrile/phosphate buffer (pH 3.5) and chromatographed on an ODS column (YMC-ODS, 2.1×25 cm, eluted with the same solvent). The fractions containing the desired compound were combined and passed through an HP-20 column. The column was washed with water and eluted with 80% acetone (pH 3). Evaporation of the eluate gave a dark red powder, which was dissolved in water (8 ml) and the solution was adjusted to pH 5.3 with 0.1 N NaOH. The resulting precipitate was collected by centrifugation, washed with acetone and dried to give a dark red powder (23.3 mg, 51%). MP>180° C. (dec). Purity by HPLC: >95%.

IR: $\nu$max (KBr) $cm^{-1}$: 3400, 1605, 1290, 1255, 1060.

UV: λmax (1/100N NaOH) nm (ε): 212(35,400), 319(15,300), 498(14,500).

$^1$H NMR: (400 MHz, DMSO-d6) 1.26 (3H, d, J=6Hz, 6'—$CH_3$), 2.32 (3H, s, Ph—$CH_3$), 2.65 (3H, s, $NCH_3$), 3.75 (2H, m, $OCH_2$), 3.91 (3H, s, $OCH_3$), 4.68 (1H, d, J=8Hz, 1'-H), 6.72 (1H, d, J=2Hz, 10-H), 6.87 (1H, s, 4-H), 7.12 (1H, d, J=2Hz, 12-H), 7.71 (1H, s, 7-H).

EXAMPLE 8

Preparation Of Desxylosyl BU-3608 FA-2

A solution of BU-3608 FA-2 (54 mg) in dioxane (5.4 ml) and 1N HCl (5.4 ml) was refluxed on a steam bath for 8 hr. The reaction mixture was diluted with water (30 ml), adsorbed on a short column of Diaion HP-20 (Mitsubishikasei, 1.8×25 cm), washed with water and eluted with 80% acetone (pH 3). The vermilion eluate was pooled and concentrated and the residue was dissolved in water (8 ml). The solution was adjusted to pH 5.3 by 0.1N NaOH and the resulting precipitate was collected by centrifugation, washed with acetone and dried in vacuo to give a dark red powder (37.7 mg 85%). MP>180° C. dec. Purity by HPLC:>95%.

IR: $\nu$max (KBr) cm$^{-1}$: 3400, 1605, 1290, 1265, 1035

UV: $\lambda$max (1/100 N NaOH)nm ($\epsilon$): 214(33,000), 234(32,300), 319(14,900), 498(14,100)

$^1$H NMR (DMSO-d$_6$) 1.15 (3H, d, J=7Hz, 6'—CH$_3$), 2.32 (3H, s, PhCH$_3$), 3.75 (2H, m, OCH$_2$), 3.91 (3H, s, OCH$_3$), 4.67 ($^1$H, d, J=8Hz,, 1'-H), 6.72 (1H, d, J=3Hz, 10-H), 6.93 (1H, s, 4-H), 7.12 (1H, d, J=3Hz, 12-H), 7.71 (1H, s, 7-H).

EXAMPLE 9

Preparation Of Desxylosyl N,N-dimethyl BU-3608 FA-2

Method A

A solution of N,N-dimethyl BU-3608 FA-2 (product of Example 6, 50 mg) in dioxane (5 ml) and 1N HCl (5 ml) was refluxed on a steam bath for 8 hr. The reaction mixture was cooled to ambient temperature and filtered to give 7.2 mg of a precipitate. The filtrate was charged on a dry silica gel column (Merck Kieselgel 60, 4×30 cm) and eluted with n-BuOH-AcOH-H$_2$O(3:1:1). The eluate was collected in 10-ml fractions. Fractions 2-14 and the precipitate earlier obtained were worked-up as described in Example 10. Fractions 21-32 were combined and charged on an HP-20 column (1.8×25 cm). The column was washed with water and eluted with 80% acetone (pH 3). Concentration of the vermilion eluate gave a solid, which was successively purified by ODS column chromatorgraphy (YMC-ODS, 2×37 cm, eluted with 20% CH$_3$CN/pH 3.5 phosphate buffer) and Diaion HP-20 chromatography (1.8×25 cm, eluted with 80% acetone at pH 3) to give 7.8 mg (17%) of the title compound as a dark red powder.

MP>180° C. (dec.) Purity by HPLC:>95%.

IR: $\nu$max (KBr) cm$^{-1}$: 3400, 1730, 1610, 1380, 1260, 1070.

UV: $\lambda$max (1/100N NaOH)nm (e): 211(38,100), 318(14,200), 496(12,500).

$^1$H NMR (DMSO-d$_6$) 1.23 (3H, d, J=7Hz, 6'-CH$_3$), 2.29 (3H, s, PhCH$_3$), 2.75 (6H, s, NCH$_3$), 3.74 (2H, m, OCH$_2$), 3.91 (3H, s, OCH$_3$), 4.60 (1H, d, J=8Hz, 1'-H), 6.73 (1H, d, J=3Hz, 10-H), 6.89(1H, s, 4-H), 7.12 (1H, d, J=3Hz, 12-H), 7.77 (1H, s, 7-H).

Method B

A solution of desxylosyl BU-3608 FA-2 (product of Example 8, 71 mg) in water (7 ml) and acetonitrile (7 ml) was adjusted to pH 7 using 0.1N NaOH. To this solution was added aqueous formaldehyde (35%, 0.3 ml) and sodium cyanoborohydride (45 mg) at room temperature. The reaction mixture was stirred overnight and the organic solvent was removed in vacuo. The aqueous residue was adjusted to pH 10 with NaOH and then added dropwise to acetone (70 ml). The precipitate was filtered off and dissolved in water at pH 2.5. The solution was charged on a column of Diaian HP-20 (1.8×25 cm), washed with water, and developed with acidic acetone (pH 3, acidified with 1N HCl). The deep red eluate was pooled, concentrated to about 5 ml, adjusted to pH 5.3 with dilute NaOH, and then added dropwise to acetone (70 ml). The resulting precipitate was collected by filtration, and re-precipitated from aqueous acetone to give 66 mg (90%) of the title compound as a dark red powder which was identical in all respects to that obtained by Method A. Purity by HPLC: >95%.

EXAMPLE 10

BU-3608 FA Aglycone

Fractions 2-14 of the eluate from the silica gel column in Example 9 (Method A) were combined and concentrated to dryness to give a powder. The powder and the precipitate of Example 9 (Method A) were dissolved in 0.01N NaOH, charged on a column of Diaion HP-20 (1.8×25 cm), washed with water and eluted with 80% acetone (pH 3). The vermilion eluate was pooled and acetone was evaporated in vacuo to give a suspension. The suspension was acidified with 1N HCl (pH 3) and extracted with butanol. Concentration of the butanol extract gave 11.5 mg of the aglycone (33%) as a dark red amorphous powder.

MP >200° C. (dec). Purity by HPLC:>95%.

IR: $\nu$max (KBr) cm$^{-1}$: 3240, 1720, 1605, 1340, 1305, 1165.

UV: $\lambda$max (1/100N NaOH) nm ($\epsilon$): 212(34,500), 319(15,200), 498(14,000).

$^1$H NMR (DMSO-d$_6$): 2.34 (3H, s, PhCH$_3$), 3.73 (2H, m, OCH$_2$), 3.91 (3H, s, OCH$_3$), 4.24 (2H, AB-q, J=11Hz, 5-H & 6-H), 4.46 (1H, m, N-CH-COOH), 6.92 (1H, d, J=2Hz, 10-H), 7.06 (1H, s, 4-$\overline{\text{H}}$), 7.28 (1H, d, J=2Hz, 12-H), 8.08 (1H, s, 7-H).

EXAMPLE 11

The general procedure described in Example 6 is followed using the reactants listed below to provide the corresponding alkylated analogs of BU-3608 FA-1 and FA-2.

| | | A + B → II. |
|---|---|---|
| A | B | II |
| BU-3608 FA-1 | acetaldehyde (1 equiv)* | $R^3$-$\beta$-D-xylosyl; $R^1$ = CH$_3$; $R^2$ = CH$_3$CH$_2$— |
| BU-3608 FA-1 | propionaldehyde (1 equiv) | $R^3$ = $\beta$-D-xylosyl; $R^1$ = CH$_3$; $R^2$ = CH$_3$CH$_2$CH$_2$— |
| BU-3608 FA-1 | acetone (1 equiv) | $R^3$ = $\beta$-D-xylosyl; $R^1$ = CH$_3$; $R^2$ = —CH(CH$_3$)$_2$ |
| BU-3608 FA-2 | acetaldehyde (2 equiv) | $R^3$ = $\beta$-D-xylosyl; $R^1$ = $R^2$ = CH$_3$CH$_2$— |
| BU-3608 FA-2 | acetone (1 equiv) | $R^3$ $\beta$-D-xylosyl; $R^1$ = H, $R^2$ = CH((CH$_3$)$_2$ |
| BU-3608 FA-2 | propionaldehyde (2 equiv) | $R^3$ = $\beta$-D-xylosyl; $R^1$ = $R^2$ = CH$_3$CH$_2$CH$_2$— |
| BU-3608 FA-2 | butyraldehyde (1 equiv) | $R^3$ $\beta$-D-xylosyl; $R^1$ = H; |

-continued

| A | B | A + B → II. II |
|---|---|---|
| Desxylosy BU-3608 FA-1 | acetaldehyde (1 equiv) | $R^2 = CH_3(CH_2)_3-$ $R^3 = H; R^1 = CH_3; R^2 = CH_3CH_2-$ |
| Desxylosy BU-3608 FA-1 | propionaldehyde (1 equiv) | $R^3 = H; R^1 = CH_3; R^2 = CH_3CH_2CH_2-$ |
| Desxylosy BU-3608 FA-1 | acetone (1 equiv) | $R^3 = H; R^1 = CH_3; R^2 = -CH(CH_3)_2$ |
| Desxylosy BU-3608 FA-2 | acetaldehyde (2 equiv) | $R^3 = H; R^1 = R^2 = CH_3CH_2-$ |
| Desxylosy BU-3608 FA-2 | acetone (1 equiv) | $R^3 = H; R^1 = H, R^2 = -CH(CH_3)_2$ |
| Desxylosy BU-3608 FA-2 | propionaldehyde (2 equiv) | $R^3 = H; R^1 = R^2 = CH_3CH_2CH_2-$ |
| Desxylosy BU-3608 FA-2 | butyraldehyde (1 equiv) | $R^3 = H; R^1 = H; R^2 = CH_3(CH_2)_3-$ |

*Minimum relative to BU-3608 reactant

We claim:

1. A process for preparing an antibiotic of Formula III

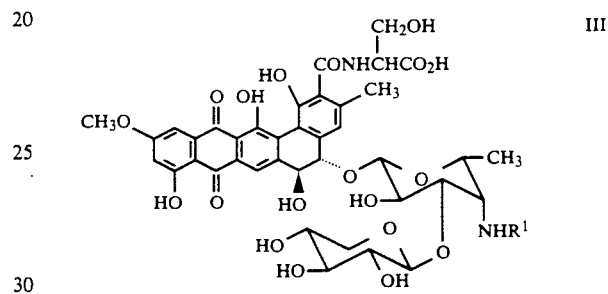

wherein $R^1$ is H or methyl, which comprises cultivating a strain of *Actinomadura hibisca* capable of producing said antibiotic in a medium containing assimilable sources of carbon and nitrogen, and D- or DL-serine under aerobic condition, and recovering said antibiotic from the cultured broth.

* * * * *